United States Patent [19]

Durant et al.

[11] 4,013,659

[45] Mar. 22, 1977

[54] CERTAIN N,N'-DISUBSTITUTED GUANIDINE COMPOUNDS AND THEIR USE

[75] Inventors: Graham John Durant; Charon Robin Ganellin, both of Welwyn Garden City; Michael Edward Parsons, St. Albans, all of England

[73] Assignee: Smith Kline & French Laboratories Limited, Welwyn Garden City, England

[22] Filed: Dec. 15, 1975

[21] Appl. No.: 640,526

Related U.S. Application Data

[63] Continuation-in-part of Ser. No. 481,716, June 21, 1974, abandoned.

[52] U.S. Cl. .................. 424/263; 260/294.8 G; 260/302 H; 260/309; 424/270; 424/273

[51] Int. Cl.² ............. C07D 403/00; C07D 417/00

[58] Field of Search ....... 260/302 H, 309, 294.8 G; 424/270, 273, 263

[56] References Cited

UNITED STATES PATENTS

| 3,736,331 | 5/1973 | Black et al. | 260/302 H |
| 3,868,457 | 2/1975 | Black et al. | 260/309 |

*Primary Examiner*—R. Gallagher
*Attorney, Agent, or Firm*—Joan S. Keps; Richard D. Foggio; William H. Edgerton

[57] ABSTRACT

N-(4-Imidazolyl)propyl-N'-heterocyclomethylthioethyl guanidines which are selective histamine $H_2$-receptor agonists.

7 Claims, No Drawings

CERTAIN N,N'-DISUBSTITUTED GUANIDINE COMPOUNDS AND THEIR USE

This application is a continuation-in-part of Ser. No. 481,716 Filed Jun. 21, 1974, now abandoned.

This invention relates to new compounds having pharmacological activity. These compounds are specific histamine $H_2$-receptor agonists. In addition, this invention relates to pharmaceutical compositions comprising these compounds and to methods for their use as specific histamine $H_2$-receptor agonists. The compounds of this invention are specific histamine $H_2$-receptor agonists (Black et al. Nature 236, 385 (1975)) and may be used for example to test the secretory action of the stomach by selectively stimulating the secretion of gastric acid. Compounds which are already available for the above purpose and which act by stimulating the secretion of gastric acid are not particularly selective in this action and thus often gives rise to distressing side effects such as skin flushing, nausea, abdominal cramps, headache, dizziness and hypotension. It is an object of the present invention to provide compounds which are more selective in their action. Diagnostic agents which stimulate the secretory action of the stomach are useful for the detection of achlorhydria and to indicate the magnitude of gastric acid secretory capacity. The compounds of this invention will normally exist as the acid addition salts but, for convenience, reference will be made throughout this specification to the parent compounds. It will be understood that hydrated salts are also within the scope of this invention. The compounds with which the present invention is concerned are represented by the following general formula:

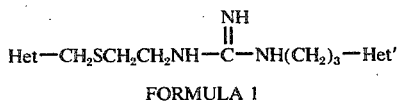

FORMULA 1 wherein Het is an optionally substituted nitrogen-containing heterocyclic ring such as a 4-imidazolyl, 5-methyl-4-imidazolyl, 5-ethyl-4-imidazolyl 5-halogeno-4-imidazolyl, 2-thiazolyl, 3-isothiazolyl, 4-halogeno-3-isothiazolyl, 2-pyridyl, 3-methyl-2-pyridyl, 3-ethyl-2-pyridyl, 3-halogeno-2-pyridyl, 3-hydroxy-2-pyridyl, 3-methoxy-2-pyridyl or 3-ethoxy-2-pyridyl ring, and Het' is a 4-imidazolyl ring Halogeno is preferably chloro or bromo. In a preferred group of compounds Het is 5-methyl-4-imidazolyl, 5-bromo-4-imidazolyl, 2-thiazolyl, 3-isothiazolyl, 3-methyl-2-pyridyl, 3-chloro-2-pyridyl or 3-methoxy-2-pyridyl ring. Compounds of Formula 1 may be produced from thioureas of Formula 2

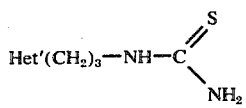

FORMULA 2 wherein Het' has the same significance as in Formula 1, by alkylation, for example with hydrogen chloride in methanol, or methyl iodide, to give an S-alkyl isothiourea of Formula 3 as a hydrohalide salt

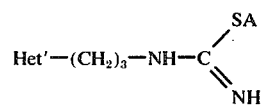

FORMULA 3 wherein A is an alkyl group, followed by treatment with an amine of Formula Het-$CH_2SCH_2CH_2NH_2$. It will be understood that an alternative procedure for the production of compounds of Formula 1 is to alkylate a thiourea of Formula 4

FORMULA 4 wherein Het is as defined in Formula 1, and treat the product with an amine Het'$(CH_2)_3NH_2$. Alternatively, compounds of Formula 1 may be produced, directly or indirectly, by reactions involving the use of a compound of Formula

FORMULA 5 wherein Q is sulphur or oxygen, A is alkyl and Y represents a group such that the compounds of Formula 7 (see below) may easily be converted into the corresponding compounds of Formula 1, for example Y may be benzoyl or cyano. Treatment of the compound of Formula 5 with an equivalent amount of the amine of formula Het-$CH_2SCH_2CH_2NH_2$ leads to the production of the intermediate of Formula 6

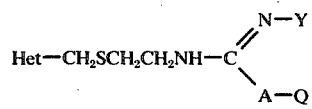

FORMULA 6

This reaction may conveniently be carried out in a solvent such as ethanol at a temperature of from 20°–100° C. Reaction of this intermediate with an amine of formula Het'-$(CH_2)_3NH_2$, wherein Het' has the same significance as in Formula 1 yields a product of Formula 7

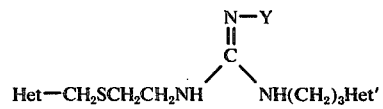

FORMULA 7

This second stage of the reaction may be conveniently carried out in the presence of or in the absence of solvent. The above mentioned second stage of the reaction may be modified when Q is sulphur by first adding to the intermediate of Formula 6 a silver salt such as silver nitrate, removing the silver alkyl mercaptide which is formed, and then proceeding with the reaction with the amine of formula Het'$(CH_2)_3NH_2$ to give a compound of Formula 7. It will be understood that an alternative procedure for the production of compounds of Formula 7 is to first react a compound of Formula 5 with an equivalent amount of an amine of formula Het'(CH$_2$)$_3$NH$_2$ to give an intermediate of Formula 8

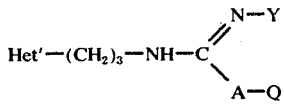

FORMULA 8 which intermediate is then treated with an amine of formula Het:CH$_2$SCH$_2$CH$_2$NH$_2$ to give a product of Formula 7. The compounds of Formula 7 are converted into compounds of Formula 1 under suitable conditions depending on the nature of Y, for example when Y is benzoyl or cyano, acid hydrolysis yields the compounds of Formula 1. As stated above, the compounds of Formula 1 are useful diagnositic agents in that they selectively stimulate the secretion of gastric acid. This action is due to the fact that these compounds are histamine H$_2$-receptor agonists, the characterisation of which is explained in detail by Black et al., Nature 1972, 236, 385. At the same time because of their selectivity the compounds possess very little histamine H$_1$-receptor agonist activity, the ratio of H$_2$- to H$_1$- agonist activity relative to histamine being at least 50 to 1. The activity of the compounds of Formula 1 may be demonstrated by their stimulation of the secretion of gastric acid from the perfused stomachs of rats anaesthetised with urethane. These compounds are given intravenously and show activity within the dose range of from 0.1 to 50 micromoles per kilogram. According to the present invention we also provide pharmaceutical compositions which comprise a compound of Formula 1, which may be in basic form or in the form of a pharmaceutically acceptable acid addition salt, together with a pharmaceutical carrier. Such addition salts include those with hydrochloric, hydrobromic, hydriodic, sulphuric and maleic acids. The active ingredient, that is the compound of Formula 1, will be present in the compositions and used in the methods of this invention in an effective amount. Preferably, each dosage unit will contain the active ingredient in an amount of from about 0.1 mg to about 50 mg most preferably from about 0.1 mg to about 5 mg. The methods of diagnosis for testing the secretory action of the stomach, according to this invention, comprise administering internally to an animal a compound of Formula 1. These compounds may be administered in basic form or in the form of a pharmaceutically acceptable acid addition salt thereof. The compounds will preferably be administered in dosage unit form as described hereabove. The invention is illustrated but no way limited by the following examples wherein temperatures are in degrees Centigrade.

EXAMPLE 1

N-[2-((5-Methyl-4-imidazolyl)methylthio)ethyl]-N'-[3-( 4-imidazolyl)-propyl] guanidine i A solution of n-[2-((5-methyl-4-imidazolyl)methylthio)ethyl]-thiourea (2.29 g) and methyl iodide (1.56 g) in methanol (5 ml) was kept at room temperature for 18 hours affordng S-methyl-N -[2-((5-methyl-4-imidazolyl)methylthio)ethyl] thiouronium iodide (2.3 g), m.p. 128°–131°. The iodide was converted into the corresponding sulphate by ion-exchange on an ion-exchange resin (IRA 401) in the sulphate form. ii. A solution of S-methyl-N-[2-((5-methyl-4-imidazolyl)methylthio)-ethyl] thiouronium sulphate (2.93 g) and 4-(3-aminopropyl) imidazole (1.25 g) in water (10 ml) was heated under reflux for 3 hours. Following concentration, the residue was converted to the free base with an ion-exchange resin (IRA 401) in the OH⁻ form and then applied to a weakly acid cation exchange resin (CG 50 in the H⁺ form) and eluted with dilute hydrochloric acid. The eluate was concentraed to give the title compound which was isolated as the tripicrate (1.8 g) m.p. 183°–185° (from acetone-water). (Found: C, 37.8; H, 3.2; N,21.8% C$_{14}$H$_{23}$N$_7$S.3 C$_6$H$_3$N$_3$O$_7$ requires: C, 38.1; H, 3.2; N,22.2%). The tripicrate was converted into the trihydrochloride salt by means of ion-exchange resin IRA 400 (Cl⁻). The tripcrate was converted into the free base by means of ion-exchange resin IRA 401 (OH⁻) and the free base was treated with oxalic acid in warm ethanol. The dioxalate crystallised on cooling and was recrystalised from aqueous etanol m.p. 125°–127°. (Found: C, 42.8; H, 5.4; N, 19.4; S, 6.3; C$_{14}$H$_{23}$N$_7$S.2 C$_2$H$_2$O$_4$ requires: C, 43.1; H, 5.4; N, 19.5; S, 6.4%)

EXAMPLE 2

N-[3-(4-Imidazolyl)propyl]-N'-[2-thiazolylmethylthio)ethyl] guanidine i. A mixture of 2-(2-thiazolylmethylthio)ethylamine dihydrochloride (3.36 g, 10 mmol), N-benzoyl dimethyldithioimidocarbonate (2.25 g, 10 mmol) and anhydrous potassium carbonate (1.38 g, 10 mmol) in methanol (25 ml) was stirred for 24 hours at room temperature, and evaporated to dryness. The residue was extracted with diethyl ether to give N-benzoyl-N'-[2-(2-thiazolylmethylthio)ethyl]-S-methyl isothiourea which was recrystallised from diethyl ether/n-hexane, m.p. 64°–65° (Found: C, 51.4; H, 4.9; N, 12.0; S, 27.1; C$_{15}$H$_{17}$N$_3$S$_3$O requires: C, 51.5; H, 4.9; N, 12.0; S, 27.4%)

ii. A mixture of N-benzoyl-N'-[2-(2-thiazolylmethylthio)ethyl]-S -methylisothiourea (8.0 g, 23 mmol) and 3-(4-imidazolyl)-propylamine (prepared from 6.51 g (23 mmol) of the dihydrobromide and sodium ethoxide) in pyridine (10 ml) was heated on a steam bath for 4 hours and evaporated. The residual oil was triturated with diethyl ether to give a solid (7.55 g) which was chromatographed on silica eluting with ethyl acetate/isopropyl alcohol to give N-benzoyl-N'-[3-(4-imidazolyl)-propyl]-N''-[2-(2-thiazolylmethylthio)ethyl]guanidine (4.76 g) mp.p. 127°–128°. (Found: C, 56.0; H, 5.5; N, 19.6; S, 14.7% C$_{20}$H$_{26}$N$_6$OS$_2$ requires: C, 56.1; H, 5.6; N, 19.6; s, 15.0%)

iii A mixture of N-benzoyl-N'-[3-(4-imidazolyl)-propyl]-N''-[2-( 2-thiazolylmethylthio)ethyl]guanidine (4.5 g) and concentrated hydrochloric acid (40 ml) was heated on a steam-bath for 6 hours and allowed to cool. The filtered mixture was diluted with water and extracted with diethyl ether. The ethereal extract was evaporated and treated with excess ethanolic picric acid and the solid formed recrystallised from acetonitrile/ethanol to give the title compound as the tripicrate m.p. 157°–158°. (Found: C, 37.0; H, 2.9; N, 20.65; S, 6.3; C$_{13}$H$_{20}$N$_6$S$_2$. 3C$_6$H$_3$N$_3$O$_7$ requires: C, 36.8; H, 2.9; N, 20.8; S, 6.3%) The tripicrate was converted into the trihydrochloride by means of ion-exchange resin IRA 400 (Cl⁻)

EXAMPLE 3

Substitution of
a. 2-(4-imidazolylmethylthio)ethylamine
b. 2-((5-bromo-4-imidazolyl)methylthio)ethylamine
c. 2-(3-isothiazolylmethylthio)ethylamine
d. 2-((4-bromo-3-isothiazolyl)methylthio)ethylamine
e. 2-(2-pyridylmethylthio)ethylamine
f. 2-((3-methyl-2-pyridyl)methylthio)ethylamine
g. 2-((3-bromo-2-pyridyl)methylthio)ethylamine
h. 2-((3-chloro-2-pyridyl)methylthio)ethylamine
i. 2-((3-hydroxy-2-pyridyl)methylthio)ethylamine
j. 2-((3-methoxy-2-pyridyl)methylthio)ethylamine (prepared by successively treating 3-hydroxy-2-hydroxymethylpyridine with methyl iodide and cysteamine)
k. 2-((3-ethoxy-2-pyridyl)methylthio)ethylamine (prepared by successively treating 3-hydroxy-2-hydroxymethylpyridine with ethyl bromide and cysteamine)
l. 2-((3-ethyl-2-pyridyl)methylthio)ethylamine (prepared by treating 3-ethyl-2-hydroxymethylpyridine with crysteamine)

for 2-(2-thiazolymethylthio)ethylamine dihydrochloride and potassium carbonate in the procedure of Example 2 leads to the production of hydrochloride salts of:
a. N-[3-(4-imidazolyl)propyl]-N'-[2-(4-imidazolymethylthio)-ethyl]guanidine
b. N-[3-(4-imidazoly)propyl]-N'-[2-((5-bromo-4-imidazolyl)-methylthio)]guanidine
c. N-[3-(4-imidazolyl)propyl]-N'-[2-(3-isothiazolyl-methylthio)-ethyl]guanidine
d. N-[3-(4-imidazolyl)propyl]-N'-[2((4-bromo-3-isothiazolyl)-methylthio)ethyl]guanidine
N-[3-(4-imidazolyl)propyl]-N'-[2-(2-pyridylmethylthio)-ethyl]guanidine
f. N-[3-(4-imidazolyl)propyl]-N'-[2-((3-methyl-2-pyridyl)methylthio)ethyl]guanidine
g. N-[3-(4-imidazolyl)propyl]-N'-[2-((3-bromo-2-pyridyl)methylthio)ethyl]guanidine
h. N-[3-(4-imidazolyl)propyl]-N'-[2-((3-chloro-2-pyridyl)methylthio)ethyl]guanidine
i. N-[3-(4-imidazolyl)propyl]-N'-[2-((3-hydroxy-2-pyridyl)methylthio-ethyl]guanidine
j. N-[3-(4-imidazolyl)propyl]-N'-[2-((3-methoxy-2-pyridyl)methylthio)-ethyl]guanidine
k. N-[3-(4-imidazolyl)propyl]-N'-[2-((3-ethoxy-2-pyridyl)methylthio)-ethyl]guanidine
l. N-[3-(4-imidazolyl)propyl]-N'-[2-((3-ethyl-2-pyridyl)methylthio)-ethyl]guanidine

EXAMPLE 4 a. (i) A solution of 2-(4-imidazolylmethylthio)ethylamine (6.0 g) and benzoyl isothiocyanate (6.0 g) in chloroform (150 ml) was heated under reflux for one hour. Concentration followed by recrystallisation from ethyl acetate-isopropyl acetate afforded N-benzoyl-N'-(2-(4-imidazolylmethylthio)-ethyl)thiourea (7.5 g). An analytically pure sample (from aqueous isopropyl alcohol) had m.p. 126°-128°.

ii. The benzoyl thiourea (6.0 g) was added to a solution of potassium carbonate (1.4 g) in water (80 ml) at 60°. The solution was maintained at this temperature for one hour, concentrated to low bulk and acidified with hydrochloric acid. Benzoic acid was removed by filtration and the filtrate was basified with potassium carbonate and concentrated under reduced pressure. Following extraction with isopropyl alcohol and concentration, the product was crystallised from isopropyl acetate. Recrystallisation from water gave N-(2-(4-imidazolylmethylthio)ethyl)thiourea (2.5 g) m.p. 135°-7°.

b. Substitution of
b. 2-((5-bromo-4-imidazolyl)methylthio)ethylamine
c. 2-(3-isothiazolylmethylthio)ethylamine
d. 2-((4-bromo-3-isothiazolyl)methylthio)ethylamine
e. 2-(2-pyridylmethylthio)ethylamine
f. 2-((3-methyl-2-pyridyl)methylthio)ethylamine
g. 2-((3-bromo-2-pyridyl)methylthio)ethylamine
h. 2-((3-chloro-2-pyridyl)methylthio)ethylamine
i. 2-((3-hydroxy-2-pyridyl)methylthio)ethylamine
j. 2-((3-methoxy-2-pyridyl)methylthio)ethylamine for 2-(4-imidazolylmethylthio)ethylamine in the above procedure and treatment of the resultant thioureas according to the general procedure of Example 1 gives
a. N-[3-(4-imidazolyl)propyl]-N'-[2-(4-imidazolymethylthio)ethyl]guanidine
b. N-[3-(4-imidazolyl)propyl]-N'-[2-((5-bromo-4-imidazolyl)-methylthio)ethyl]guanidine
c. N-[3-(4-imidazolyl)propyl]-N'-[2-(3-isothiazolyl-methylthio)ethyl]guanidine
d. N-[3-(4-imidazolyl)propyl]-N'-[2((4-bromo-3-isothiazolyl)-methylthio)ethyl]guanidine
e. N-[3-(4-imidazolyl)propyl]-N'-[2-(2-pyridylmethylthio)-ethyl]guanidine
f. N-[3-(4-imidazolyl)-N'-[2-((3-methyl-2-pyridyl)-methylthio)ethyl]guanidine
g. N-[3-(4-imidazolyl)propyl]-N'-[2-((3-bromo-2-pyridyl)-methylthio)ethyl]guanidine
h. N-[3-(4-imidazolyl)propyl]-N'-[2-((3-chloro-2-pyridyl)-methylthio)ethyl]guanidine
i. N-[3-(4-imidazolyl)propyl]-N'-[2-((3-hydroxy-2-pyridyl)methylthio)ethyl]guanidine
j. N-[3-(4-imidazolyl)propyl]-N'-[2-((3-methoxy-2-pyridyl)methylthio)ethyl]guanidine

EXAMPLE 5

By dissolving 0.5 mg of N-[2-((5-methyl-4-imidazolyl)methylthio)ethyl]-N'-[3-(4-imidazolyl)-propyl]guanidine trihydrochloride in 2 ml of sterile water or normal saline solution a pharmaceutical composition for parenteral administration is produced. In the same way solutions of the compounds produced according to any one of Examples 2 to 4 may be produced.

What we claim is:
1. A compound of the formula

wherein Het is a 4-imidazolyl, 5-methyl-4-imidazolyl, 5-ethyl-4-imidazolyl, 5-halogeno-4-imidazolyl, 2-thiazolyl, 3-isothiazolyl, 4-halogeno-3-isothiazolyl, 2-pyridyl, 3-methyl-2-pyridyl, 3-ethyl-2-pyridyl, 3-halogeno-2-pyridyl, 3-hydroxy-2-pyridyl, 3-methoxy-2-pyridyl or 3-ethoxy-2-pyridyl ring, and Het' is a 4-imidazole ring; or a hydrate or pharmaceutically acceptable salt or hydrated salt thereof.

2. A compound of claim 1 wherein Het is a 5-methyl-4-imidazolyl, 5-bromo-4-imidazolyl, 2-thiazolyl, 3-isothiazolyl, 3-methyl-2-pyridyl, 3-chloro-2-pyridyl or 3-methoxy-2-pyridyl ring, or a hydrate or pharmaceutically acceptable salt or hydrated salt thereof.

3. A compound of claim 1, said compound being N-[2-((5-methyl-4-imidazolyl)methylthio)ethyl]-N'-[4-imidazolyl)propyl]-guandine, or a hydrate or pharmaceutically acceptable salt or hydrated salt thereof.

4. A compound of claim 1, said compound being N-[2-(2-thiazolylmethylthio)ethyl]-N'-[3-(4-imidazolyl)guanidine, or a hydrate or pharmaceutically acceptable salt or hydrated salt thereof.

5. pharmaceutical composition to selectively stimulate histamine $H_2$-receptors comprising an effective amount to stimulate said receptors of a compound of claim 1 in combination with a pharmaceutically acceptable diluent or carrier.

6. A method of selectively stimulating histamine $H_2$-receptors which comprises administering a compound of claim 1 parenterally to an animal in an amount sufficient to stimulate said receptors.

7. A method of diagnosing gastric secretory activity which comprises administering a compound of claim 1 parenterally to an animal in an amount sufficient to stimulate said activity.

* * * * *

UNITED STATES PATENT AND TRADEMARK OFFICE
CERTIFICATE OF CORRECTION

PATENT NO. : 4,013,659

DATED : March 22, 1977

INVENTOR(S) : Graham John Durant, Charon Robin Ganellin and Michael Edward Parsons It is certified that error appears in the above-identified patent and that said Letters Patent are hereby corrected as shown below:

On the first page of the patent, in the left-hand column, following item [63] insert the following:

[30]  July 13, 1973        United Kingdom 33428/73
      December 20, 1974    United Kingdom 55122
      December 20, 1974    United Kingdom 55123

Column 1, line 14, "(1975)" should read -- (1972) -- .

Column 3, line 17, "Het:$CH_2SCH_2CH_2NH_2$" should read

-- Het-$CH_2SCH_2CH_2NH_2$ -- .

Column 7, line 8, "[4-imidazolyl)" should read
-- [3-(4-imidazolyl) -- .

Signed and Sealed this twelfth Day of July 1977

[SEAL]

Attest:

RUTH C. MASON
*Attesting Officer*

C. MARSHALL DANN
*Commissioner of Patents and Trademarks*